United States Patent [19]

Quinn et al.

[11] Patent Number: 4,921,138
[45] Date of Patent: May 1, 1990

[54] DEVICE FOR ADMINISTRATION OF ENTERAL FLUIDS FROM PRE-FILLED SHAPE RETENTIVE CONTAINERS

[75] Inventors: David G. Quinn, Grayslake; Robert B. Edwards, II, Libertyville; Erik Andersen, Vernon Hills, all of Ill.

[73] Assignee: Corpak, Inc., Wheeling, Ill.

[21] Appl. No.: 226,380

[22] Filed: Jul. 29, 1988

Related U.S. Application Data

[63] Continuation-in-part of Ser. No. 144,526, Nov. 15, 1988, abandoned.

[51] Int. Cl.⁵ .............................................. B67B 7/24
[52] U.S. Cl. ...................................... 222/85; 222/155; 222/181; 222/185; 222/189; 222/478; 222/541; 248/231.14; 248/316.4; 604/260; 604/411
[58] Field of Search ..................... 222/80, 81, 83.5, 85, 222/86, 88, 105, 155, 158, 159, 49, 50, 180, 181, 183, 185, 189, 475, 478, 481, 481.5, 541; 294/22, 103.1, 902, 34; 248/311.2, 313, 318, 231.4, 316.4; 604/262, 405, 406, 246, 257, 260, 411, 414; 141/329, 330; 220/284, 278, 18, 450, 454, 458, 461

[56] References Cited

U.S. PATENT DOCUMENTS

| | | | |
|---|---|---|---|
| 2,986,142 | 5/1961 | Bieberdorf et al. | 604/262 |
| 3,108,717 | 10/1963 | Kindseth | 222/89 |
| 3,229,678 | 1/1966 | Anspach | 222/155 X |
| 3,311,267 | 3/1967 | Lee et al. | 222/155 |
| 3,311,268 | 3/1967 | Fields | 222/181 X |
| 3,902,932 | 9/1975 | Gdanski et al. | 248/313 |
| 4,085,866 | 4/1978 | Fekl | 222/158 |
| 4,201,208 | 5/1980 | Cambio, Jr. | 604/411 |
| 4,269,332 | 5/1981 | Conn | 222/475 |
| 4,411,661 | 10/1983 | Kersten | 222/81 X |
| 4,684,038 | 8/1987 | Gaul et al. | 222/475 X |
| 4,699,296 | 10/1987 | Schrock, Jr. | 222/181 X |
| 4,753,639 | 6/1988 | Iwatschenko | 604/262 X |
| 4,798,605 | 1/1989 | Steiner et al. | 604/411 |

FOREIGN PATENT DOCUMENTS

| | | |
|---|---|---|
| 1264317 | 3/1968 | Fed. Rep. of Germany . |
| 3611112 | 7/1987 | Fed. Rep. of Germany ...... 604/260 |

Primary Examiner—Kevin P. Shaver
Assistant Examiner—Gregory L. Huson
Attorney, Agent, or Firm—Wallenstein, Wagner & Hattis, Ltd.

[57] ABSTRACT

An improved device for aspetic dispensing of enteral feeding solutions from shape retentive, pre-filled containers. The device including a distensible hanger member formed around only the end panels of the container to suspend the container in an orientation to define only a single uppermost corner and a single lowermost corner. The device further including corner attachment members for firmly securing a therapeutic fluid dispensing column only to the uppermost and lowermost corners of the container. The fluid dispensing column having venting and dispensing spikes. The spikes having an outer configuration which forms leak-proof seals with an aperture formed in the container. The spikes further including an arrangement of laterally opposed inlet ports joined to a large diameter axial bore.

23 Claims, 5 Drawing Sheets

DEVICE FOR ADMINISTRATION OF ENTERAL FLUIDS FROM PRE-FILLED SHAPE RETENTIVE CONTAINERS

REFERENCE TO RELATED APPLICATION

This is a continuation-in-part application of Ser. No. 07/144,526, filed Jan. 15, 1988 and now abandoned.

TECHNICAL FIELD

The present invention generally relates to fluid dispensing devices in the field of enteral nutritional feeding, and, in particular, to an improved device for aseptic dispensing of enteral fluids or other medical or nutritional fluids from a sealed, shape retentive container.

BACKGROUND ART

Enteral nutrition is achieved through naso-esophageal intubation of a feeding tube. Typically, the enteral feeding tube is joined to a distensible container, such as a flexible bag similar to that disclosed in U.S. Pat. No. 4,529,102. Several disadvantages may be encountered through the use of enteral feeding bags, chief of which is that the fluid administration system is an open, rather than closed system. That is, because pre-filled enteral feeding bags are difficult to ship, deliver and store, the user is required to fill the bag with enteral nutritional solution before initiating enteral therapy. The handling of the enteral solutions by users often led to potentially septic fluid administration conditions. Hence, in order to develop a closed administration system, it has become important to consider administering enteral nutritional solutions from a sealed, pre-filled, shape retentive container.

One such container which has been successfully utilized in enteral feeding therapy is a shape retentive paperboard carton disclosed in U.S. Pat. No. 4,287,247 and sold under the trademarks TETRA PAK, TETRA BRIK, and BRIK PAK. Such cartons are pre-filled with enteral nutritional fluid and then sealed. However, in using such paperboard cartons in the administration of enteral solutions, it is necessary to utilize a device which can aseptically access the fluid contents of the carton and deliver such fluids at a controlled rate.

One such device is disclosed in U.S. Pat. No. 4,699,296. However, this fluid dispensing device for paperboard cartons has inherent disadvantages. One such disadvantage is that this device requires a rigid cradle structure to support and suspend the carton in a particular angular orientation in which the carton has a single uppermost corner and a single lowermost corner. This cradle is expensive to manufacture and complicates set up of an enteral feeding administration system.

In addition, the dispensing device disclosed in U.S. Pat. No. 4,669,296 includes a fluid dispensing column which is secured to the carton merely by the insertion of dispensing spikes, carried on the column, into apertures on the cradle. Securement of the fluid dispensing column is achieved only by the frictional engagement of the spikes into the puncture holes of the carton. As a result, it is possible for the fluid dispensing column to become disengaged during enteral administration causing leakage or spillage and an inaccurate administration of enteral nutritional solutions.

Figures 11, 12, 13:
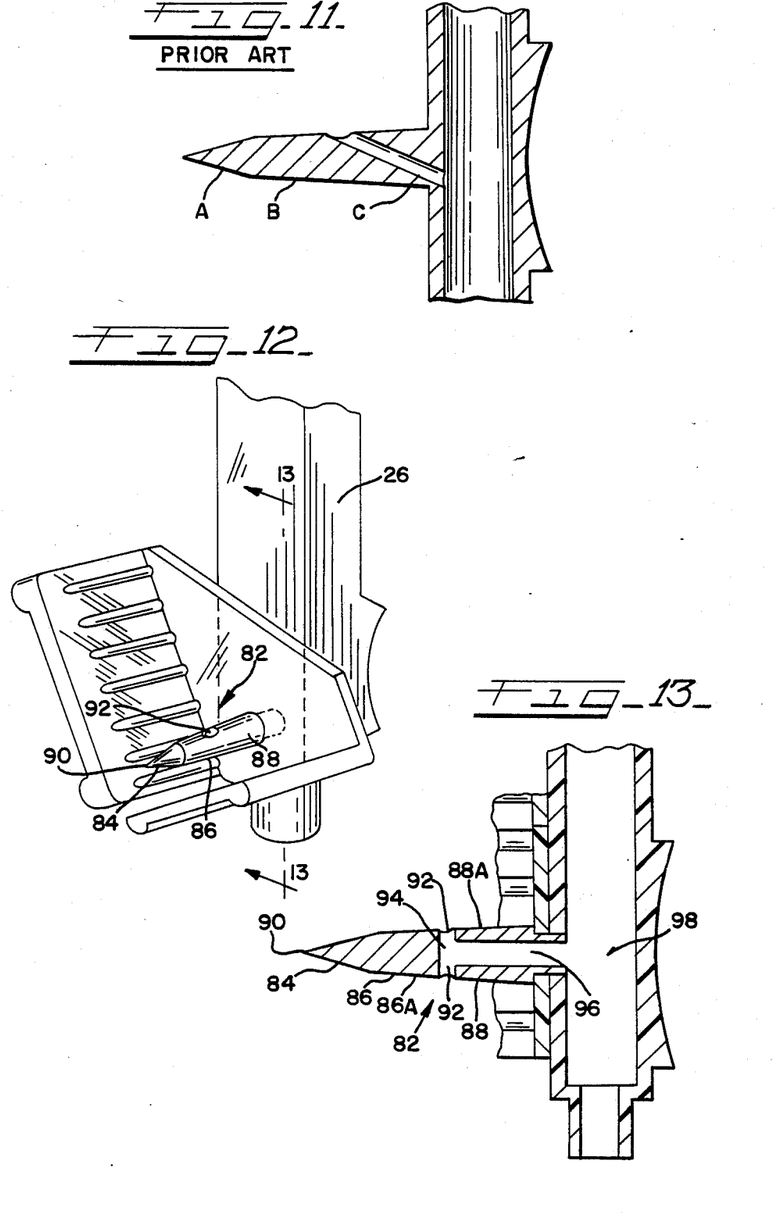

In addition, the prior art fluid dispensing column disclosed in U.S. Pat. No. 4,699,296 utilizes two dispensing spikes, each positioned near the upper and lower ends of the column. Such prior art spikes have a configuration and structure as disclosed in FIG. 11. The prior art spike is conical from the base of the spike to the point of the spike. In addition, the prior art spike includes a single inlet port located about mid-way along the side wall of the spike. The aperture is in fluid communication with an inner bore having the same diameter as the inlet port and angularly extending into a lumen of the fluid dispensing column as shown in FIG. 11. Because of the use of a single inlet port and a bore, both having limited inner diameters, the prior art dispensing spike restricted fluid flow, thereby resulting in fluid flow rate problems.

Despite restricted fluid flow properties, no fluid leakage problems are encountered upon full penetration and insertion of the spike of FIG. 11 into a shape retentive container. This is believed to be a result of the use of a conical spike tip having an axially centered point which permits a centered penetration of the shape retentive container. As a result of such centered penetration, the container material is turned inwardly to form a uniform margin which circumferentially surrounds the spike. This uniform margin or collar creates a fluid seal which prevents fluid leakage upon full insertion and penetration of the spike into the container. However, because the prior art spike disclosed in FIG. 11 is conical from the point of the spike to the base, leakage results if the spike is slightly withdrawn from the aperture formed in the container. Due to the inclined walls of the base of the spike, a breach of the fluid seal between the margin and the spike itself occurs virtually immediately upon any withdrawal of the spike resulting in substantial fluid leakage.

Hence, prior to the present invention, a need existed for a device for aseptic access and dispensing of enteral feeding fluids from a shape retentive, pre-filled container, such as a BRIK PAK carton, in which proper hanging of the carton can be achieved without the use of rigid cradle structures and permitting a secure attachment of a fluid dispensing column to the container.

A need also existed for a fluid dispensing column for use in penetrating shape retentive containers which utilizes dispensing spikes that maximize fluid flow, utilize centered penetration to eliminate fluid leakage upon full penetration and insertion of the spike into the container and employs an outer spike configuration to avoid fluid leakage from slight, inadvertent withdrawal of the spike from the aperture in the container.

SUMMARY OF THE INVENTION

According to the present invention, an improved device for aseptic dispensing of enteral feeding fluids from shape retentive, pre-filled containers has been developed which avoids use of rigid cradle structures for suspending the container. Instead, one embodiment of the present invention uses a distensible hanger member formed around only the end panels of the container to suspend the container in an orientation to define only a single uppermost corner and a single lowermost corner. The hanger member may be applied to the container after pre-filling and sealing of the container so that the user receives the container with the hanger member ready for use.

Another embodiment of the present invention utilizes a rigid hanger member having a pocket joined to a tab with an aperture, in an angular configuration to suspend the container in the orientation defining a single uppermost corner and a single lowermost corner. The pocket of the rigid hanger member receives the corner fold from one end panel of the container to suspend the container in the required orientation. The corner fold utilized by the rigid hanging member is a result of the construction of the shape retentive carton, particularly those in paperboard cartons manufactured in accordance with U.S. Pat. No. 4,287,247. Such cartons are formed by folding and adhering a single sheet of container material. One of the results of such container construction is at least one corner fold formed from an end panel of the container in which the fold is adhered onto an adjacent end panel. In order to utilize the rigid hanger member, it is necessary to detach the corner fold from the end panel to which it is adhered and to pull the corner fold upward in order to permit the insertion of the corner fold into the pocket of the rigid hanger member.

The present invention also utilizes unique corner attachment members for firmly securing a fluid dispensing column, having venting and dispensing spikes, only to the uppermost and lowermost corners of the container.

Finally, the present invention preferably utilizes dispensing spikes having improved container penetration and fluid flow characteristics yet minimize fluid leakage. Generally, the preferred overall configuration of the spike of the present invention includes a conical portion having an axial penetration point. Integrally formed with the conical tip portion is a body portion having side walls less angularly inclined than the side walls of the conical tip portion. Preferably integrally formed with the body portion is a base portion having parallel wall defining a generally cylindrical configuration. As will be explained later in greater detail, this overall spike configuration forms a fluid seal with the inward margins of the aperture in the container to virtually eliminate fluid leakage.

In addition, the improved spike of the present invention also utilizes laterally opposed fluid inlet ports which define an inlet bore bisecting the longitudinal axis of the spike. This inlet bore perpendicularly joins an axial bore of larger inner diameter. As a result, fluid flow rates are dramatically improved over prior art fluid dispensing spikes.

Other advantages and aspects of the invention will become apparent upon making reference to the specification, claims, and drawings to follow.

BRIEF DESCRIPTION OF DRAWINGS

FIG. 11 discloses in vertical section a dispensing spike utilized in prior art fluid dispensing columns;

FIG. 12 discloses in perspective view an improved dispensing spike utilized in the present invention; and, FIG. 13 is a vertical section taken along line 13—13 of FIG. 12.

DETAILED DESCRIPTION

While this invention is susceptible of embodiment in many different forms, there is shown in the drawings and will be described in detail a preferred embodiment of the invention. The present disclosure is to be considered only as an exemplification of the principles of the invention and is not intended to limit the broad aspect of the invention to embodiment illustrated.

Figures 1, 1A:
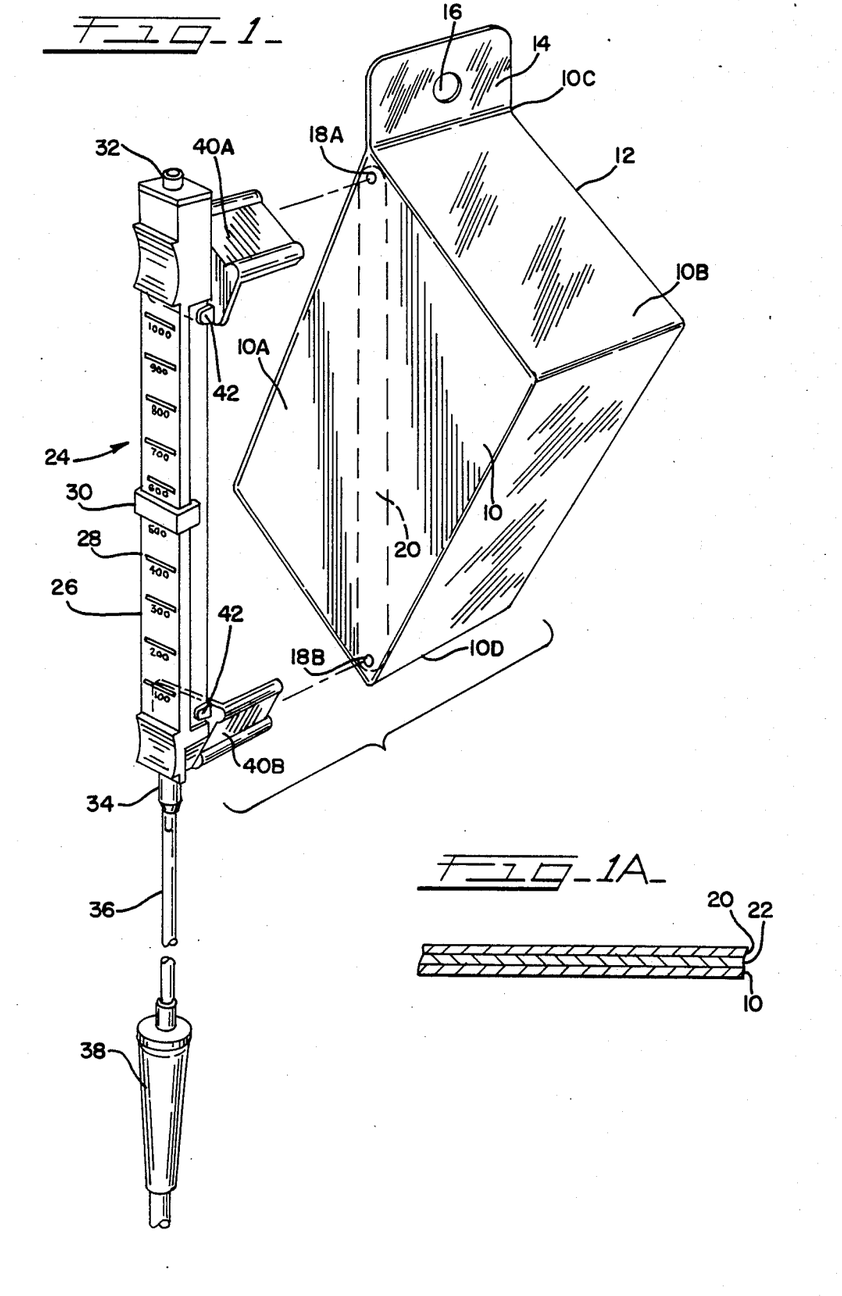
FIG. 1 discloses in an exploded perspective view a preferred embodiment of the present invention.
FIG. 1A discloses in fragmented section a portion of a shape retentive container having a two-sided adhesive layer thereon affixed to which is a releasable tab or strip.

Referring now to the drawings, FIG. 1 discloses a sealed shape retentive container 10, pre-filled with an enteral feeding solution. Container 10 preferably is of a paperboard-type construction such as the cartons marketed under the trademark BRIK PAK made by Tetra Pak International, Inc. The construction of such cartons permits easy penetration of the carton walls with fluid dispensing spikes, as will be discussed later in greater detail. Container 10 has at least two side walls which may also be termed face panels 10A and, depending on the configuration of the container, a plurality of end panels or side panels 10B.

In order to suspend container 10 in an orientation suitable for administration of enteral fluids, a distensible hanger 12 is wrapped around end panels 10B. Hanger 12 has a suspending tab 14 having an aperture 16 to receive a portion of a support post. Hanger 12 suspends container 10 in a manner to define a single uppermost corner 10C and a single lowermost corner 10D. The importance of this orientation to the effective administration of enteral feeding solutions will be explained below.

Figures 2, 3, 4, 5:
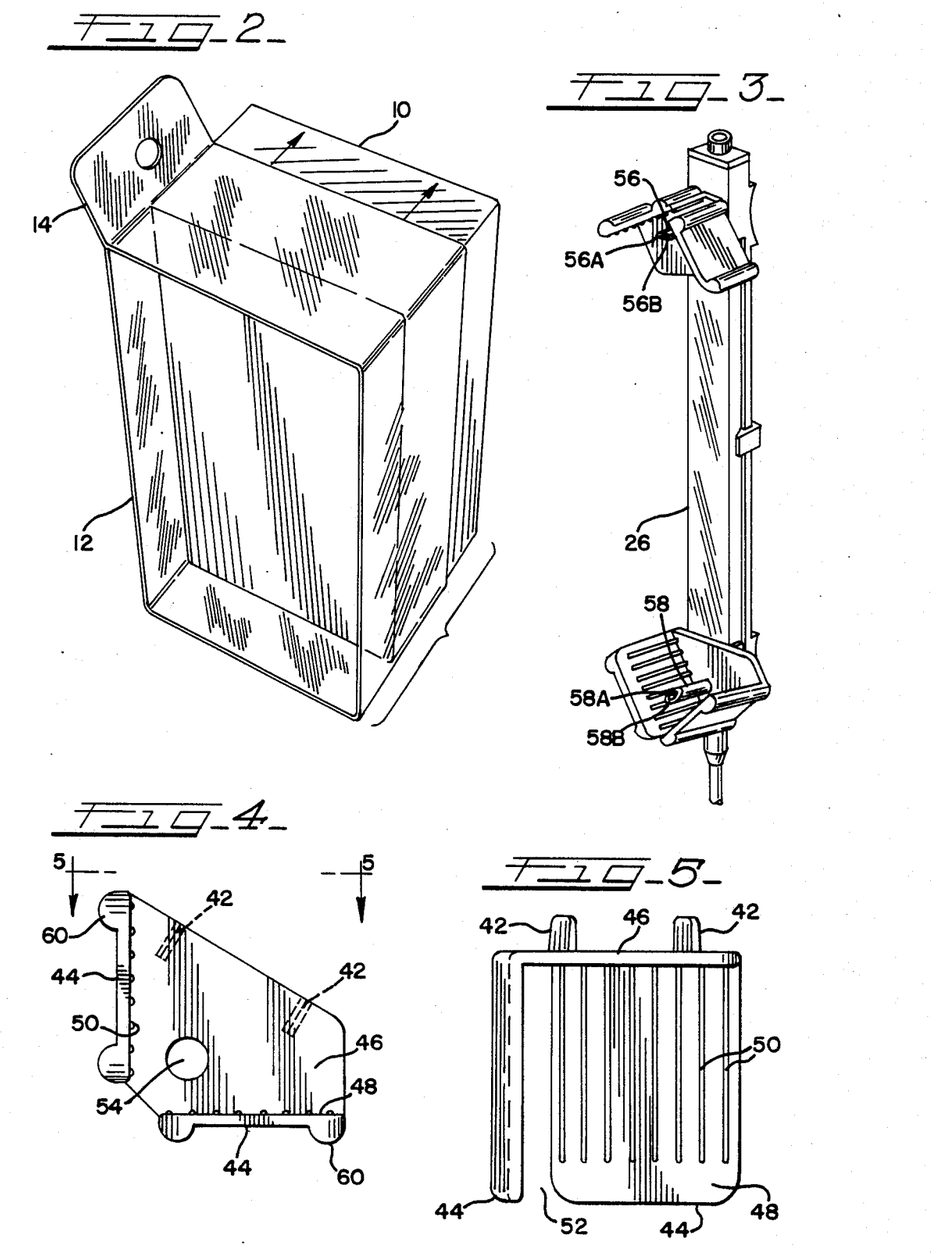
FIG. 2 discloses the manner in which a preferred embodiment of a distensible hanger member is formed around the end panels of a pre-filled enteral feeding container.
FIG. 3 discloses a backside perspective view of a preferred embodiment of a fluid dispensing column of the present invention.
FIG. 4 discloses a side elevational view of a preferred embodiment of a corner attachment member.
FIG. 5 is a view of the corner attachment member taken along line 5—5 of FIG. 4.
Figure 6:
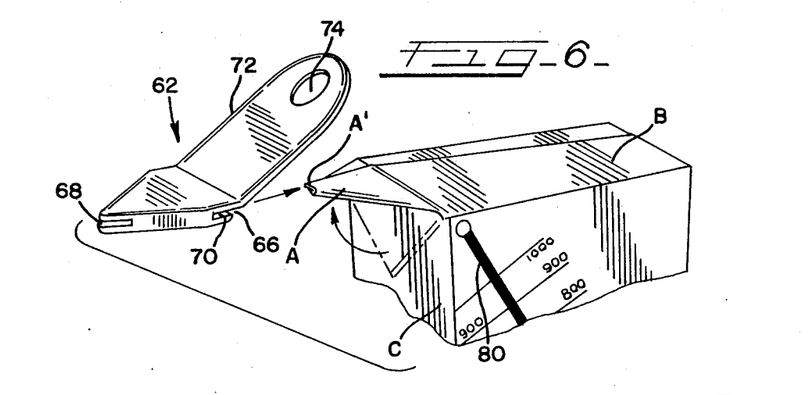
FIG. 6 is a perspective view disclosing an alternative embodiment of a hanger member.
Figure 7A:
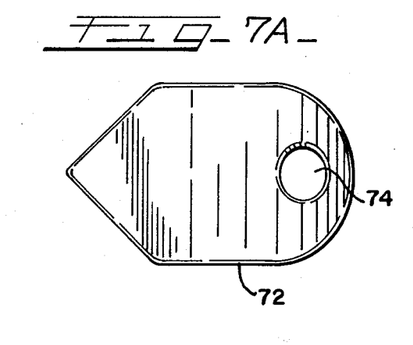
FIG. 7A is a plan view of the alternative embodiment of a hanger member.
Figure 7B:
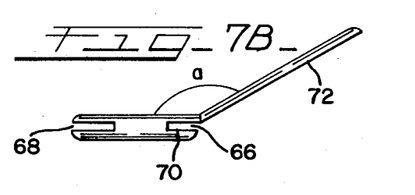
FIG. 7B is a side elevation of the hanger member embodiment of FIG. 7A.
Figure 7C:
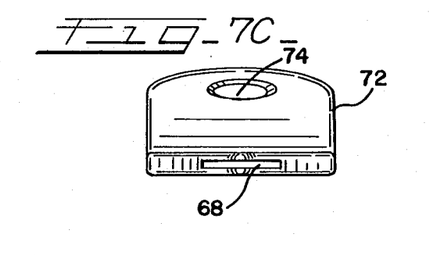
FIG. 7C is a front elevation of the embodiment of the hanger member disclosed in FIG. 7A.

Hanger 12 may be made from polyvinyl chloride or other plastic material which can be shrink wrapped to container 10 by application of heat. As best disclosed in FIG. 2, hanger 12 is initially slightly oversized to permit hanger 12 to easily fit around each end panel 10B of container 10. Heat is applied to hanger 12 to tightly shrink and stretch hanger 12 on container 10. As a result, hanger 12 is tightly formed onto the container 10. This allows container 10 to be shipped and delivered to an end user with hanger 12 already formed onto the container. In an alternative embodiment, hanger 12, and specifically suspending tab 14, could be made from the treated paperboard material comprising container 10 so as to form an integral part of the construction of container 10.

In order to access the contents of container 10, dispensing spikes must penetrate aperture puncture areas 18A and 18B which may be either pre-formed or created by penetrating with the spikes. Areas 18A and 18B are initially covered by a releasable strip 20 which can be removed from container 10 to reveal puncture areas 18A and 18B. Areas 18A and 18B may also be covered by two individual tabs covering only the immediate area around the aperture areas.

As disclosed in FIG. 1A, beneath removable strip or tab 20 is a two-sided adhesive layer 22, preferably made of plastic, which is adhered to container 10. The underside of tab 20 is a smooth release liner surface so that tab 20 can be easily removed from layer 22. As will be later described in greater detail, adhesive layer 22 is an important element in acheiving leak-free apertures in container 10.

FIG. 1 discloses the required orientation of suspending container 10 with hanger 12 in order to achieve optimal administration of enteral fluids. Specifically, aperture area 18A is located proximate to uppermost corner 10C and aperture area 18B is located proximate to lowermost corner 10D. By this orientation of container 10, the fluid level within container 10 is slightly below aperture area 18A so that aperture area 18A becomes a vent to allow influx of ambient air pressure to facilitate outflow of fluid from aperture 18B.

FIG. 1 also discloses a fluid dispensing device 24 comprised of a hollow fluid dispensing column 26 which preferably is transparent to permit visualization of fluid within column 26 for use of volumetric graduations 28 and a slidable measure 30. At an upper end of column 26 is a venting port 32 to dispose column 26 to ambient air pressure. At a lower end of column 26 is a fluid dispensing port 34 joined to a segment of administration set tubing 36 interposed along which is a drip chamber 38 of the type commonly known in the art.

Dispensing device 24 further includes at least two unique corner attachment members 40A and 40B which are preferably secured to column 26 by tabs 42. As best disclosed in FIGS. 4 and 5, corner attachment members 40 include at least two legs 44 which are perpendicular to each other and a brace member 46 joining the legs 42 together. An inner surface 48 of each of legs 44 preferably include a plurality of ribs 50 which facilitate securement of the corner attachment members 40 to the uppermost corner and lowermost corner of container 10. In a preferred embodiment, an elongated channel 52 is formed at the apical intersection of legs 44. Channel 52 further facilitates securement of corner attachment members 40 to container 10 and, with respect to uppermost corner 18A, permits passage of suspending tab 14.

In each corner attachment member 40, an aperture 54 is positioned proximate to channel 52. As disclosed in FIG. 3, aperture 54 permits passage of a spike 56 which has a venting function through uppermost corner aperture 18A, and a spike 58 which has a fluid dispensing function through lowermost corner 18B. In the preferred embodiment of the present invention as disclosed in FIG. 3, corner members 40 are affixed to dispensing device 24 such that spike 56 passes through uppermost corner member 40A and spike 58 passes through lowermost corner member 40B. Each of spikes 56, 58 are positioned a pre-selected distance corresponding to the spacing of aperture areas 18A and 18B on container 10. Further, each of spikes 56 and 58 have internal passageways which are in fluid communication with fluid dispensing column 26. Spikes 56 and 58 have axially offset penetrating tips 56A and 58A and axial fluid bores 56B and 58B. Finally, FIG. 4 discloses an embodiment of corner attachment members 40 including rounded peripheral edges 60 for firmly gripping each of members 40 when penetrating the spikes into the container.

FIGS. 6 through 10 disclose an alternate embodiment of a hanger member 62 and a fluid dispensing column 64. Hanger member 62 may only be used with shape retentive cartons which are formed by folding and adhering a single sheet of container material, such as the construction utilized to form a BRIK PAK or TETRA PAK carton referred to above. As disclosed in FIG. 6, for pre-filled shape retentive cartons having this construction, at least one corner fold A is formed and extends from an end panel B. Corner fold A normally is folded downward and adhered to an adjacent end panel C. However, to utilize rigid hanger member 62, corner fold A is detached and bent or folded outwardly in the manner disclosed in FIG. 6. Corner fold A is then inserted into a pocket 66 of hanger 62. Pocket 66 has inner dimensions so as to tightly secure corner tab A within pocket 66. Pocket 66, in a preferred embodiment, has an overall triangular configuration coinciding with the configuration of corner fold A. However, the configuration of pocket 66 may be altered to correspond with any other configuration of a corner fold. As best disclosed in FIGS. 7B and 7C, pocket 66 is provided with an apical slit 68 which permits apex A' of corner fold A to seat within apical slit 68 to assure that corner fold A fully and tightly seats within pocket 66. Lateral slits 70 provided near the opening of pocket 66 perform the same function as apical slit 68.

Rigid hanger 62 also includes a rigid hanger tab 72 which is provided with an aperture 74 to engage an arm of a vertical suspension stand. In order for hanger 62 to suspend a container by corner fold A in an orientation to properly define a single uppermost corner and a single lowermost corner, tab 72 and pocket 66 must be angularly joined in an angle "a" (FIG. 7B) ranging from 120° to 150° and preferably 135°.

Figure 8:
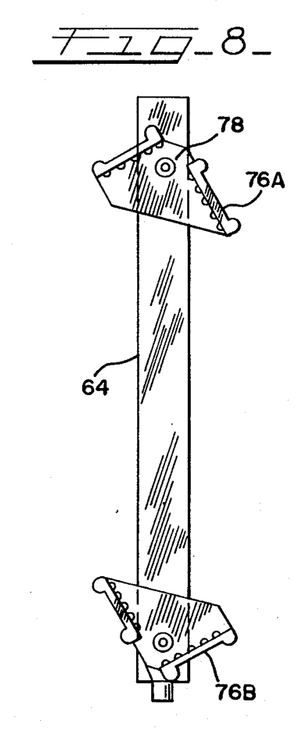
FIG. 8 is a rear elevational view of the fluid dispensing column and corner members utilized with the alternate embodiment member hanger.

FIG. 8 discloses corner members 76A/76B which are utilized with hanger member 62. Corner members 76A, 76B have the same general configuration and structure as corner members 40A and 40B which are used with distensible hanger 12. The primary distinction between the construction of corner members 76A and 76B with corner members 40A and 40B is that upper corner member 76A must have a larger apical opening 78 in order to accommodate pocket 66 of hanger 62.

Figure 9:
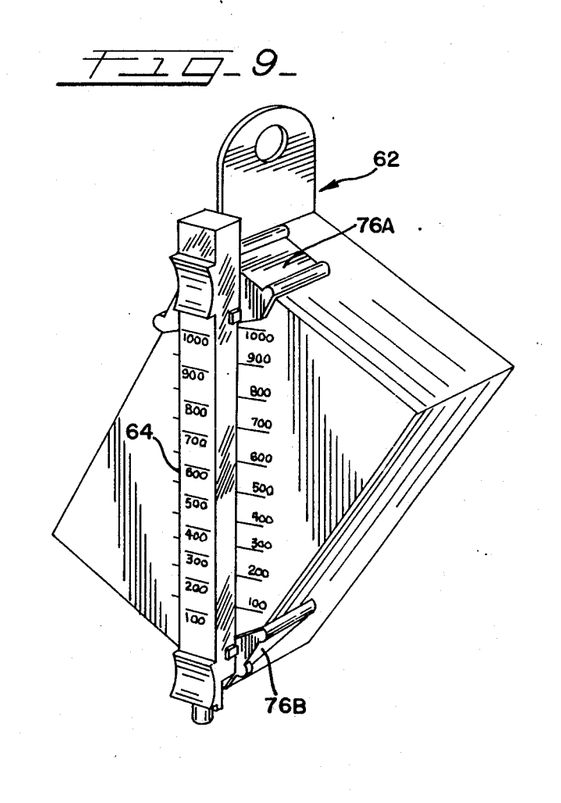
FIG. 9 is a perspective view disclosing attachment of alternate embodiment of the hanger member and fluid dispensing column.

FIG. 9 discloses the attachment of fluid column 64 and hanger 62 to suspend a container in an orientation defining a single uppermost corner and a single lowermost corner. In addition, FIG. 9 also discloses the use of at least one linear vertical arrangement of volumetric graduations imprinted on a side panel of the container and arrangement parallel to fluid dispensing column 64.

Figure 10:
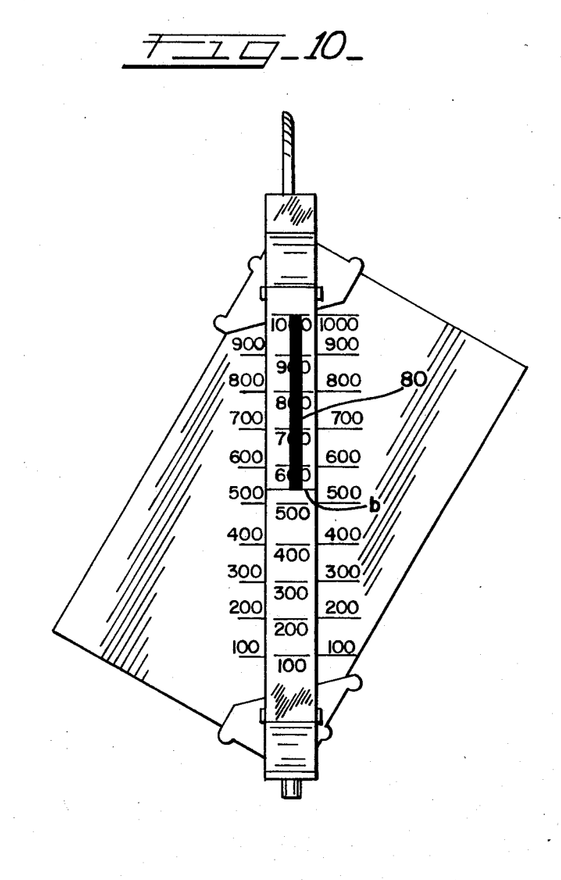
FIG. 10 is a front view of the invention disclosed in FIG. 9.

Likewise, FIG. 10 discloses imprinting linear vertical arrangements of volumetric graduations along each side of fluid dispensing column 64. In addition, FIG. 10 also discloses imprinting onto a side panel of the container a linear indicia 80 which is longitudinally aligned with fluid dispensing column 64. Further, linear indicia 80 should be color contrasting with both the side panel of the container as well as the visual appearance of the therapeutic fluid carried within fluid dispensing column 64. Linear indicia 80 is visible through transparent fluid dispensing column 64 and may be used to visually ascertain the meniscus "b" of the fluid within column 64. By comparing meniscus "b" with the volume graduations on column 64 or the volumetric graduations imprinted upon the container, a user can easily determine the volume of fluid contents of the container.

Finally, FIGS. 12 and 13 disclose an improved structure and configuration of dispensing spikes. The improved overall configuration of a dispensing spike 82 disclosed in FIGS. 12 and 13 is preferably utilized for both the upper and lower spikes of the fluid dispensing column 26. As disclosed in FIG. 12, dispensing spike 82 is comprised of a conical tip portion 84, a body portion 86 having side walls 86A which are less angularly inclined than the side walls of tip portion 84 and, a generally cylindrically shaped base portion 88 having linear and parallel side walls 88A. Preferably, tip portion 84, body portion 86 and base portion 88 are integrally molded into a single spike, but could also be manufactured from individually formed parts and then bonded together.

Unlike the prior art dispensing spike disclosed in FIG. 11 in which the spike tip portion A, body portion B and base portion C define an overall conical configuration from point to base, spike 82 has a highly conical outer configuration at tip portion 84, a less conical outer configuration at body portion 86 and non-conical or cylindrical configuration at base portion 88. The use of conical and non-conical configurations in a dispensing spike impart several distinct advantages with respect to the penetration and formation of leak-free apertures in a shape retentive container. By utilizing an axially centered point 90 on conical tip portion 84, a centered penetration aperture results. That is, as point 90 penetrates the container and spike 82 is inserted into the container, the side walls of conical tip portion 84 rapidly widens the initial penetration to begin forming an aperture. As base portion 86 passes into the aperture, the aperture continues to widen and portions of the container side wall are inwardly directed to create a margin or collar from the adhesive layer 22 adhered to container 10. This margin of adhesive layer 22 is of uniform size and dimension and circumferentially surrounds the spike 82. As a result of these uniform dimensions and the adhesive properties of layer 22, a fluid seal is formed between the side walls of spike 82 and the adhesive margin. In addition, the remaining external surface of adhesive layer 22 serves to adhere the fluid dispensing column 26 on to container 10. Where the point of the spike is axially offset, as shown, for example, in tip 58A of spike 58 in FIG. 3, the margin or collar is non-uniform in size and dimensions and results in fluid leakage.

Unlike base portion C of the prior art dispensing spike disclosed in FIG. 11, base portion 88 of spike 82 has a non-conical almost cylindrical configuration with generally linear and parallel side walls 88A. An advantage of this outer configuration of base portion 88 is that unlike the prior art spike of FIG. 11, during aperture formation, widening of the aperture ceases upon reaching base portion 88. In the event spike 82 is inadvertently slightly withdrawn from the aperture, fluid leakage is avoided as the margin of the aperture formed from a part of adhesive layer 22 surrounds base portion 88 and remains in adhesive contact with side walls 88A. That is, when spike 82 is slightly withdrawn from the aperture, the adhesive margin pulls outward with the spike to prevent leakage. On the other hand, in the prior art dispensing spike disclosed in FIG. 11, during aperture formation, base portion C continues widening the aperture because of the angular side walls of base portion C. As a result, any slight withdrawal of the spike from the aperture immediately breaks the fluid seal formed between the non-adhesive margin of the aperture and the base portion side walls. Therefore, as a result of the axially centered penetrating point 90, a highly conical tip portion 84 in combination with non-conical base portion 88, spike 82 forms a leak-proof seal with the adhesive margin of the aperture both when the spike is inserted into the container as well as upon inadvertent slight withdrawal of the spike from the container aperture.

Another advantage of the structure of improved dispensing spike 82 is the use of laterally opposed fluid inlet ports 92. Ports 92 preferably are generally positioned at the base portion 88 of spike 82 but may also be positioned at the junction of body portion 86 and base portion 88. Ports 92 define a lateral bore 94 which is perpendicular to the longitudinal axis of spike 82. Lateral bore 94 is perpendicularly joined and in fluid communication with an axial bore 96 having an inner diameter which is preferably greater than the inner diameter of lateral bore 94 thereby further enhancing fluid flow. Axial bore 96 empties into a main lumen 98 of fluid dispensing column 26. By utilizing laterally opposed inlet ports 92 joined to a larger axial bore 96, fluid flow efficiency is enhanced relative to a single inlet port joined to a single angular inlet bore as disclosed in the prior art dispensing spike of FIG. 11. Hence, dispensing spike 82 not only minimizes fluid leakage, but also enhances fluid flow relative to prior art dispensing spikes.

While the specific embodiments have been illustrated and described, numerous modifications come to mind without significantly departing from the spirit of the invention and the scope of protection is only limited by the scope of the accompanying claims.

We claim:

1. A device for aseptic dispensing of therapeutic fluids from a shape retentive container having a plurality of corners, two opposing face panels and a plurality of side panels, comprising:

distensible and formable hanger means for suspending the container in such an orientation to define one uppermost corner and one lowermost corner, the hanger means being wrapped and formed around only the side panels of the container;

means for dispensing therapeutic fluid from the container, said dispensing means having at least an uppermost spike for penetrating the container near the uppermost corner and a lowermost spike for penetrating the container near the lowermost corner, said spikes each having an axial bore being in fluid communication through an enclosed passage in the dispensing means, the uppermost spike venting ambient air into the container through an upper end of the passage, the lowermost spike dispensing fluid out of the container through a lower end of the passage; and, one corner member for attachment to only the uppermost corner of the container, an other corner member detached from the one corner member, the other corner member for attachment to only the lowermost corner of the container, each of said corner members being carried on the means for dispensing therapeutic fluid, the uppermost spike passing through the one corner member, the lowermost spike passing through the other corner member.

2. The device for aseptic dispensing of therapeutic fluids from a shape retentive container described in claim 1 wherein the distensible hanger means wraps around only the side panels of the container.

3. The device for aseptic dispensing of therapeutic fluids from shape retentive containers described in claim 1 wherein one face panel of the container includes:
   at least one removable segment for concealing areas of one face panel for inserting a spike; and
   a two-sided adhesive layer adhered to the area of one face panel and underneath the removable segment.

4. The device for aseptic dispensing of therapeutic fluids from shape retentive containers described in claim 3 wherein the one face panel of the container includes one removable tab concealing an area near the uppermost corner of the container and an other removable tab concealing an area near the lowermost corner of the container.

5. The device for aseptic dispensing of therapeutic fluids from a shape retentive container described in claim 1 wherein each corner member includes two legs being in an angular orientation corresponding to the angle defined by the corner of the container, the legs each having an inner surface for abutting against a portion of the side panels of the carton proximate to the corner, the legs being joined to each other by at least one brace member, each corner member having an apex defined by the intersection of the legs, the spikes for penetrating the uppermost corner and lowermost corner of the carton being positioned proximate to the apex of each corner member.

6. The device for aseptic dispensing of therapeutic fluids from a shape retentive container described in claim 5 wherein the inner surface of each leg includes ribs for facilitating insertion of the uppermost corner and lowermost corner into each corner member.

7. The device for aseptic dispensing of therapeutic fluids from a shape retentive container described in claim 5 wherein the brace member includes an opening to permit passage of the spike.

8. The device for aseptic dispensing of therapeutic fluids from a shape retentive container described in claim 1 wherein the fluid passage includes a transparent tubular column.

9. The device for aseptic dispensing of therapeutic fluids from a shape retentive container described in claim 8 wherein the container includes:
   graduated volumetric indicia positioned parallel to the tubular column.

10. The device for aseptic dispensing of therapeutic fluids from a shape retentive container described in claim 8 wherein the container includes:
    columnar indicia being applied to the container and visible through the tubular column, the indicia being color contrasting to the therapeutic fluid to permit a user to ascertain the volume of fluid within the container by aligning the meniscus of fluid within the column with a volumetric marking of the columnar indicia.

11. The device for aseptic dispensing of therapeutic fluids from shape retentive containers described in claim 8 wherein an uppermost end of the tubular column carries a filtered vent for screening debris from ambient air.

12. The device for aseptic dispensing of therapeutic fluids from shape retentive containers described in claim 1 wherein the uppermost spike and the lowermost spike each include:
    a conical tip portion for initially forming an aperture in the container, the tip portion having side walls defining an axially centered point;
    a body portion joined to the tip portion, the body portion having side walls less angularly inclined than the side walls of the conical portion;
    a generally cylindrical base portion joined to the body portion, the base portion having an axial bore for passing fluid into the channel; and
    a plurality of fluid inlet ports positioned near the junction of body portion and the base portion, the ports being in fluid communication with the axial bore of the base portion.

13. The device for aseptic dispensing of therapeutic fluids from shape retentive containers described in claim 12 wherein the conical tip portion, the body portion and the base portion are integrally formed to define a unitary spike structure.

14. The device for aseptic dispensing of therapeutic fluids from shape retentive containers described in claim 12 wherein the inlet ports are positioned in the base portion.

15. The device for aseptic dispensing of therapeutic fluids from shape retentive containers described in claim 12 wherein the inlet ports are in fluid communication with a lateral bore, the lateral bore being perpendicular to and in fluid communication with the axial bore in the base portion.

16. A device for aseptic dispensing of therapeutic fluids from a shape retentive container having a plurality of corners, two opposing face panels and a plurality of side panels, comprising:
    means for suspending the container in such an orientation to define one uppermost corner and one lowermost corner, the suspending means being wrapped and formed around the container without contacting the two opposing face panels of the container;
    means for dispensing therapeutic fluid from the container, said dispensing means having at least an uppermost spike for penetrating the container near the uppermost corner and a lowermost spike for penetrating the container near the lowermost corner, said spikes each having an axial bore being in fluid communication through an enclosed passage, the uppermost spike venting ambient air into the container through an upper end of the passage, the lowermost spike dispensing fluid out of the container through a lower end of the passage; and,
    one corner member for attachment to only the uppermost corner of the container, an other corner member detached from the one corner member, the other corner member for attachment to only the lowermost corner of the container, each of said corner members being carried on the dispensing means, the uppermost spike passing through the one corner member, the lowermost spike passing through the other corner member.

17. The device for aseptic dispensing of therapeutic fluids from shape retentive containers described in claim 16 wherein the uppermost spike and the lowermost spike each include:
    a conical tip portion for initially forming an aperture in the container, the tip portion having side walls defining an axially centered point;
    a body portion joined to the tip portion, the body portion having side walls less angularly inclined than the side walls of the conical portion;

a generally cylindrical base portion joined to the body portion, the base portion having an axial bore for passing fluid into the channel; and a plurality of fluid inlet ports positioned near the junction of body portion and the base portion, the ports being in fluid communication with the axial bore of the base portion.

18. A device for aseptic dispensing of therapeutic fluids from a shape retentive container having a plurality of corners, two opposing face panels and a plurality of side panels, the container being formed by folding and adhering a sheet of container material, the container having at least one corner fold extending from one end panel and being normally adhered onto an adjacent side panel, the one corner fold may be detached from the adjacent side panel and bent outward, comprising:

hanger means for suspending the container in such an orientation to define one uppermost corner and one lowermost corner, the hanger means suspending the container only from the detached one corner fold;

means for dispensing therapeutic fluid from the container, said dispensing means having at least an uppermost spike for penetrating the container near the uppermost corner and a lowermost spike for penetrating the container near the lowermost corner, said spikes each having an axial bore being in fluid communication through an enclosed passage in the dispensing means, the uppermost spike venting ambient air into the container through an upper end of the passage, the lowermost spike dispensing fluid out of the container through a lower end of the passage; and, one corner member for attachment to only the uppermost corner of the container, an other corner member detached from the one corner member, the other corner member for attachment to only the lowermost corner of the container, each of said corner members being carried on the means for dispensing therapeutic fluid, the uppermost spike passing through the one corner member, the lowermost spike passing through the other corner member.

19. The device for aseptic dispensing of therapeutic fluids from a shape retentive container described in claim 18 wherein the hanger means includes:

a rigid hanger having a pocket for receiving the one corner fold and a tab member having an aperture, the pocket and tab member being joined in a relative angular configuration to suspend the container in said orientation defining one uppermost corner and one lowermost corner.

20. The device for aseptic dispensing of therapeutic fluids from shape retentive containers described in claim 18 wherein the uppermost spike and the lowermost spike each include:

a conical tip portion for initially forming an aperture in the container, the tip portion having side walls defining an axially centered point;

a body portion joined to the tip portion, the body portion having side walls less angularly inclined than the side walls of the conical portion;

a generally cylindrical base portion joined to the body portion, the base portion having an axial bore for passing fluid into the channel; and a plurality of fluid inlet ports positioned near the junction of body portion and the base portion, the ports being in fluid communication with the axial bore of the base portion.

21. The device for aseptic dispensing of therapeutic fluids from shape retentive containers described in claim 20 wherein the conical tip portion, the body portion and the base portion are integrally formed to define a unitary spike structure.

22. The device for aseptic dispensing of therapeutic fluids from shape retentive containers described in claim 20 wherein the laterally opposed inlet ports are positioned in the base portion.

23. The device for aseptic dispensing of therapeutic fluids from shape retentive containers described in claim 20 wherein the laterally opposed inlet ports are in fluid communication with a lateral bore, the lateral bore being perpendicular to and in fluid communication with the axial bore in the base portion.

* * * * *